United States Patent
Sloman et al.

(10) Patent No.: US 8,121,688 B2
(45) Date of Patent: Feb. 21, 2012

(54) METHOD AND SYSTEM FOR AUTOMATICALLY SWITCHING BETWEEN MODES OF AN IMPLANTABLE MEDICAL DEVICE

(75) Inventors: Laurence S. Sloman, West Hollywood, CA (US); Jeffery D. Snell, Chatsworth, CA (US)

(73) Assignee: Pacestter, Inc., Sylmar, CA (US)

( * ) Notice: Subject to any disclaimer, the term of this patent is extended or adjusted under 35 U.S.C. 154(b) by 442 days.

(21) Appl. No.: 12/483,995

(22) Filed: Jun. 12, 2009

(65) Prior Publication Data

US 2010/0318153 A1    Dec. 16, 2010

(51) Int. Cl.
*A61N 1/37* (2006.01)

(52) U.S. Cl. ............................... 607/28; 607/27
(58) Field of Classification Search ............... 607/27–28, 607/9, 4
See application file for complete search history.

(56) References Cited

U.S. PATENT DOCUMENTS

| | | | |
|---|---|---|---|
| 5,766,229 A | 6/1998 | Bornzin | |
| 6,038,474 A * | 3/2000 | Zhu et al. | 607/9 |
| 6,615,089 B1 | 9/2003 | Russie et al. | |
| 6,928,326 B1 | 8/2005 | Levine | |
| 6,950,704 B1 | 9/2005 | Bradley | |
| 6,963,775 B2 | 11/2005 | Russie et al. | |
| 6,973,350 B1 | 12/2005 | Levine et al. | |
| 7,006,869 B2 | 2/2006 | Bradley | |
| 7,035,687 B1 | 4/2006 | Levine et al. | |
| 7,286,876 B2 | 10/2007 | Yonce et al. | |
| 7,412,287 B2 | 8/2008 | Yonce et al. | |
| 2003/0083711 A1* | 5/2003 | Yonce et al. | 607/27 |
| 2004/0148109 A1 | 7/2004 | Fischer | |
| 2006/0149328 A1 | 7/2006 | Parikh et al. | |
| 2006/0224193 A1 | 10/2006 | Hess | |

FOREIGN PATENT DOCUMENTS

WO  2006069032 A1  6/2006
WO  2007073514 A1  6/2007

OTHER PUBLICATIONS

Kam, Ruth, "Automatic Capture Verification in Pacemakers (Autocapture)—Utility and Problems," Indian Pacing Electrophysioly J. Apr.-Jun. 2004:;4(2):73-78.

* cited by examiner

*Primary Examiner* — Carl H Layno
*Assistant Examiner* — Paula J Stice

(57) ABSTRACT

An implantable medical device includes a lead, a pulse generator, an autocapture module, an autothreshold module, a fusion detection module, and a control module. The lead includes electrodes configured to be positioned within a heart. At least one of the electrodes is capable of sensing cardiac signals. The pulse generator delivers a stimulus pulse through at least one of the electrodes. The autocapture module senses an evoked response of the heart after delivery of the stimulus pulse when operating in an autocapture mode. The autothreshold module performs a threshold search when operating in an autothreshold mode. The fusion detection module identifies fusion-based behavior in the heart. The control module automatically switches between the autothreshold and autocapture modes based on a presence of the fusion-based behavior.

20 Claims, 8 Drawing Sheets

METHOD AND SYSTEM FOR AUTOMATICALLY SWITCHING BETWEEN MODES OF AN IMPLANTABLE MEDICAL DEVICE

CROSS-REFERENCE TO RELATED APPLICATIONS

This application is related to co-pending U.S. patent application Ser. No. 12/483,976, filed concurrently herewith, titled "Method and System for Overdriving a Heart Chamber During a Threshold Search".

FIELD OF THE INVENTION

Embodiments of the present invention generally pertain to implantable medical devices and more particularly to methods and systems that adjust the electrical potential of stimulus pulses applied to a heart during delivery of pacing and/or shocking therapies to the heart.

BACKGROUND OF THE INVENTION

An implantable medical device (IMD) is implanted in a patient to monitor, among other things, electrical activity of a heart and to deliver appropriate electrical therapy, as required. Implantable medical devices include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. These pulses are referred to as stimulus or stimulation pulses.

The stimulus pulses are delivered to chambers of the heart at a stimulus output. The stimulus output represents the strength or electrical potential of the stimulus pulses. If the stimulus output of the pulses is not sufficiently large, then the stimulus pulses may be ineffective. Stimulus pulses having an output that does not exceed a stimulation threshold of the heart may not cause polarization of one or more chambers of the heart or propagate. For example, a stimulus pulse applied to an atrium at a stimulus output that is less than the stimulation threshold of the heart may not result in depolarization of the atrium, or capture in the atrium.

In order to ensure that the stimulus pulses are delivered to the heart at a sufficiently high stimulus output, the IMD may monitor and adjust the electrical potential of the stimulus pulses on a beat-by-beat basis. In one operational mode referred to as an autocapture mode, the IMD applies a stimulus pulse to a ventricle of the heart and monitors the evoked response of the ventricle. If the stimulus pulse results in capture in the ventricle, or ventricular contraction, then the IMD does not adjust the electrical potential of subsequent stimulus pulses. On the other hand, if the stimulus pulse does not result in ventricular capture, then the IMD increases the electrical potential of subsequent stimulus pulses. This monitoring of the evoked response occurs on a beat-by-beat basis in known IMDs. That is, some known IMDs may adjust the electrical potential of a stimulus pulse applied in a cardiac cycle based on the evoked response in the preceding cardiac cycle(s).

During the autocapture mode, a back-up stimulus pulse may be applied when capture is not detected. For example, if capture is not detected in a ventricle within a predetermined time period after delivering a ventricular stimulus pulse, some known IMDs supply a back-up stimulus pulse to the ventricle to ensure ventricular contraction during the current cardiac cycle. If a stimulus is delivered at approximately the same time as an intrinsic cardiac event, fusion may occur. The fusion of intrinsic and paced ventricular contractions may cause the IMD to adjust the electrical potential of the stimulus pulses too frequently. For example, fusion can cause a captured ventricular contraction to appear as a non-captured ventricular contraction caused by a ventricular stimulus pulse. The appearance of a captured contraction as a non-captured contraction may result in the IMD increasing the electrical potential of subsequent stimulus pulses, even though the current electrical potential of the pulses is sufficient to induce capture. As a result, the IMD unnecessarily wastes electrical energy of the IMD. Alternatively, a non-captured ventricular contraction caused by a ventricular stimulus pulse may appear as a captured ventricular contraction. As a result, the IMD may not increase the electrical potential of subsequent stimulus pulses, even though the current electrical potential may be insufficient to induce capture.

Additionally, some known IMDs cause a threshold search to be performed when a predetermined number of consecutive cardiac cycles exhibit a loss of capture. The threshold search involved incrementally decreasing the electrical potential of the stimulus pulses applied to the heart until a predetermined number of consecutive cardiac cycles demonstrate a loss of capture. The electrical potential of the pulses is then incrementally increased until a predetermined number of consecutive cardiac cycles exhibit capture. In situations where fusion causes captured contractions to appear as non-captured contractions, the IMD may unnecessarily initiate a threshold search. The repeated application of stimulus pulses during a threshold search can cause patient discomfort, compromise hemodynamics, and waste battery energy. Therefore, unnecessary threshold searches may result in unnecessary patient discomfort and decreased device longevity.

A need exists for an improved IMD and method of operating an IMD that enables the adjustment of the electrical potential of stimulus pulses while reducing the number of back-up stimuli and threshold searches due to the occurrence of fusion.

BRIEF SUMMARY OF THE INVENTION

In one embodiment, an implantable medical device is provided. The implantable medical device includes a lead, a pulse generator, an autocapture module, an autothreshold module, a fusion detection module, and a control module. The lead includes electrodes configured to be positioned within a heart. At least one of the electrodes is capable of sensing cardiac signals. The pulse generator delivers a stimulus pulse through at least one of the electrodes. The autocapture module senses an evoked response of the heart after delivery of the stimulus pulse when operating in an autocapture mode. The autothreshold module performs a threshold search when operating in an autothreshold mode. The fusion detection module identifies fusion-based behavior in the heart. The control module automatically switches between the autothreshold and autocapture modes based on a presence of the fusion-based behavior.

In another embodiment, a method for automatically switching between autocapture and autothreshold modes in an implantable medical device is provided. The method includes delivering a stimulus pulse to a heart and identifying fusion-based behavior in the heart in response to the stimulus pulse. The method also includes automatically switching between the autocapture and autothreshold modes based on a presence of the fusion-based behavior. When in the autocapture mode, the method includes sensing an evoked response after delivery of a stimulus pulse. When in the autothreshold mode, the method includes performing a threshold search.

In another embodiment, a computer readable storage medium for an implantable medical device is provided. The implantable medical device includes a lead with electrodes configured to be positioned within a heart to sense cardiac signals, a pulse generator, and a microcontroller. The computer readable storage medium includes instructions to direct the pulse generator to deliver a stimulus pulse to the heart. The instructions also direct the microcontroller to identify fusion-based behavior in the heart in response to the stimulus pulse and automatically switch between an autocapture mode and an autothreshold mode based on a presence of the fusion-based behavior. When in the autocapture mode, the instructions direct the microcontroller to sense an evoked response after delivery of the stimulus pulse. When in the autothreshold mode, the instructions direct the microcontroller to perform a threshold search.

BRIEF DESCRIPTION OF THE DRAWINGS

The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided for automatically switching an implantable medical device between an autocapture mode and an autothreshold mode based on fusion-based behavior of a heart. When the implantable medical device is in the autocapture mode, the device may sense an evoked response of the heart after delivery of a stimulus pulse to the heart on a beat-by-beat basis and optionally perform a threshold search. When the device is in the autothreshold mode, the device may perform a threshold search. The sensing of the evoked response and the threshold search may independently be used to adjust the electrical potential of subsequent stimulus pulses delivered to the heart.

Figure 1:
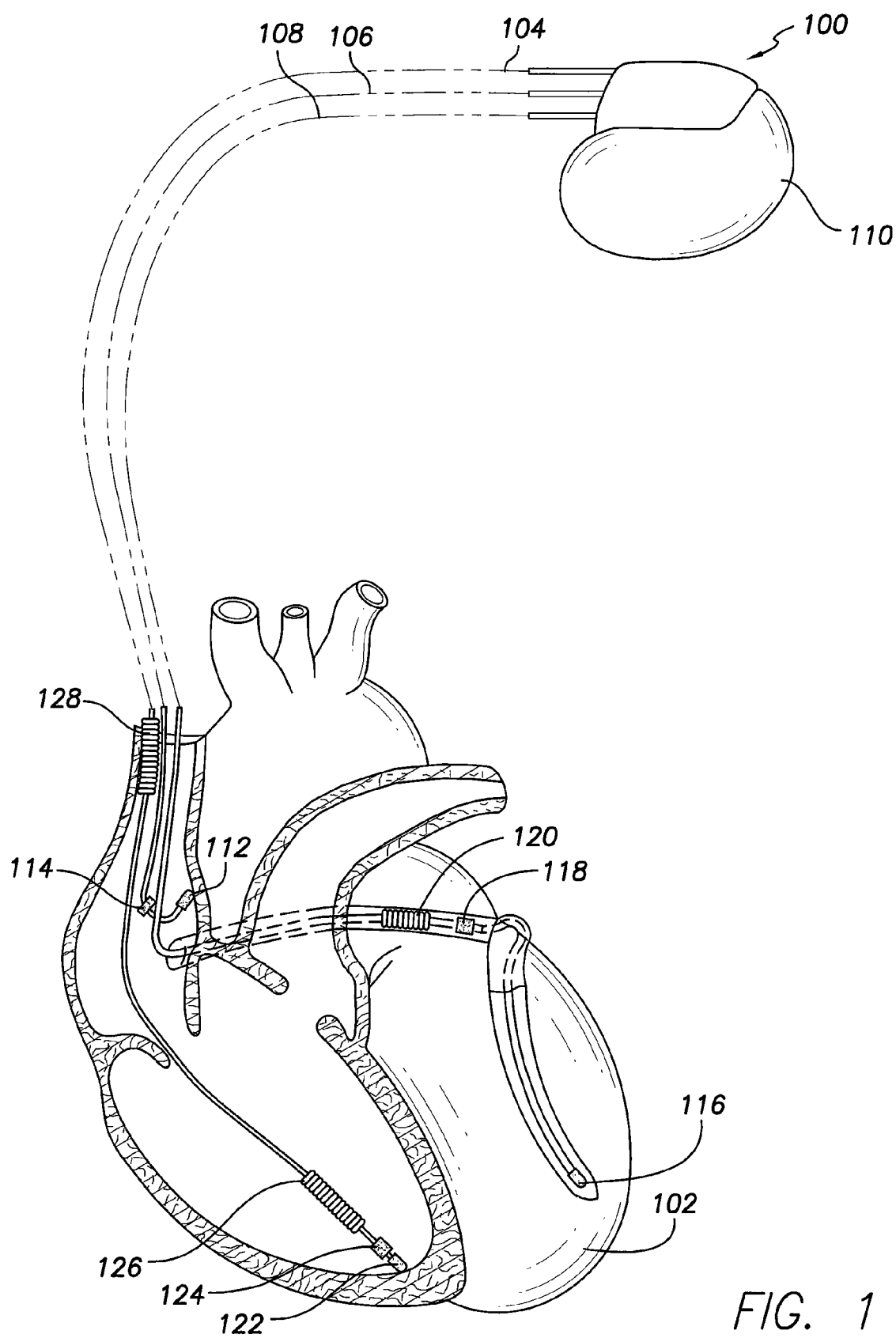
FIG. 1 illustrates an implantable medical device (IMD) coupled to a heart in accordance with one embodiment.

FIG. 1 illustrates an implantable medical device (IMD) 100 coupled to a heart 102 in accordance with one embodiment. The IMD 100 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like. The IMD 100 includes a housing 110 that is joined to several leads 104, 106, 108. The leads 104, 106, 108 are located at various locations of the heart 102, such as an atrium, a ventricle, or both, to measure cardiac signals of the heart 102. The leads 104, 106, 108 include the right ventricular (RV) lead 104, the right atrial (RA) lead 106, and the coronary sinus lead 108. Several electrodes are coupled with the leads 104, 106, 108 for sensing cardiac signals and/or for delivering stimulus or stimulation pulses to the heart 102. The housing 110 may be one of the electrodes and is often referred to as the "can", "case", or "case electrode."

The RV lead 104 is coupled with an RV tip electrode 122, an RV ring electrode 124, and an RV coil electrode 126. The RV lead 104 may include a superior vena cava (SVC) coil electrode 128. The right atrial lead 106 includes an atrial tip electrode 112 and an atrial ring electrode 114. The coronary sinus lead 108 includes a left ventricular (LV) tip electrode 116, a left atrial (LA) ring electrode 118 and an LA coil electrode 120. Alternatively, the coronary sinus lead 108 may be a quadropole lead that includes several electrodes disposed within the left ventricle. Leads and electrodes other than those shown in FIG. 1 may be included in the IMD 100 and positioned in or proximate to the heart 102.

The IMD 100 monitors cardiac signals of the heart 102 to determine if and when to deliver stimulus pulses to one or more chambers of the heart 102. The IMD 100 may deliver pacing stimulus pulses to pace the heart 102 and maintain a desired heart rate and/or shocking stimulus pulses to treat an abnormal heart rate such as tachycardia or bradycardia. The stimulus pulses are supplied to the heart 102 at a stimulus output. The stimulus output is the magnitude or strength of the stimulus pulses. For example, a stimulus output may represent the electric potential of a stimulus pulse. The stimulus output needs to be periodically checked and/or updated to ensure that the stimulus output exceeds a stimulation threshold. The stimulation threshold represents the minimum stimulus output required to capture the stimulus pulse in one or more chambers of the heart. The stimulation threshold may be an intrinsic characteristic of the heart 102 that changes over time. A stimulus pulse delivered to an atrium of the heart at an electric potential that exceeds the stimulation threshold of the heart 102 may propagate through the heart 102 to a corresponding ventricle and be captured in the ventricle to cause polarization or contraction of the ventricle. Conversely, a stimulus pulse delivered at a stimulus output that does not exceed the stimulation threshold may not be captured in the ventricle to cause ventricular contraction.

In order to ensure that stimulus pulses are delivered to the heart 102 at electric potentials that exceed the stimulation threshold of the heart 102, the IMD 100 may periodically adjust the stimulus output of the pulses. The IMD 100 automatically switches between at least two modes to adjust the stimulus output of the pulses. One mode is referred to as an autocapture mode. In the autocapture mode, the IMD 100 monitors an evoked response of the heart 102 after delivery of a stimulus pulse to determine if the stimulus pulse results in capture in another chamber of the heart 102. The IMD 100 may supply a stimulus pulse to the ventricle of the heart 102 and monitor the evoked response of the ventricle to determine if the pulse resulted in ventricular capture. If the stimulus pulse resulted in ventricular capture, then the IMD 100 does not adjust the stimulus output of subsequent stimulus pulses. On the other hand, if the stimulus pulse does not result in ventricular capture, then the IMD 100 may apply a back-up stimulus pulse to the ventricle to cause ventricular contraction. The IMD 100 also increases the stimulus output of subsequent stimulus pulses. In the autocapture mode, the application of the pulse and the monitoring of the evoked response occur in a single cardiac cycle and may be repeated for each of multiple cardiac cycles. For example, in the autocapture mode, the IMD 100 may monitor beat-by-beat variations in the evoked response and adjust the stimulus output of subsequent pulses in a beat-by-beat manner. Thus, the electric potential of the stimulus pulses can vary in each of several consecutive cardiac cycles.

Another mode in which the IMD 100 may adjust the stimulus output of stimulus pulses is referred to as an autothreshold mode. In the autothreshold mode, the IMD 100 performs a threshold search that adjusts the electric potential of stimulus pulses applied to the heart 102 after the threshold search is completed. The threshold search adjusts the stimulus output of the pulses such that the pulses have an output that is at least as great as the stimulation threshold. In one embodiment, a threshold search incrementally decreases the electric potential of pulses in consecutive cardiac cycles until a predetermined number of consecutive losses of capture are detected. For example, the stimulus output at which stimulus pulses are applied to an atrium of the heart 102 may be decreased by 0.25 or 0.3 Volts for each cardiac cycle until a loss of capture in the corresponding ventricle is detected. If a loss of capture is detected in a cardiac cycle, the IMD 100 may deliver a back-up stimulus pulse to the ventricle to ensure ventricular contraction during the cardiac cycle. Once the loss of capture is detected, the same stimulus output is used for the next cardiac cycle to determine if another loss of capture occurs. If the loss of capture continues to occur for the predetermined number of consecutive cardiac cycles, then the losses of capture may indicate that the current stimulus output is below the stimulation threshold. In one embodiment, the predetermined number of consecutive cardiac cycles is two. Alternatively, if the loss of capture does not occur in the following cardiac cycle, the stimulus output continues to be decreased in subsequent cardiac cycles until loss of capture occurs in the predetermined number of consecutive cardiac cycles.

Once the stimulus output is decreased such that loss of capture occurs for the predetermined number of cardiac cycles, the stimulus output is then incrementally increased. The stimulus output is increased for each cardiac cycle until capture is detected. For example, the stimulus output may be increased by 0.125 or 0.3 Volts for each cardiac cycle until capture is detected. Additional stimulus pulses are applied at the current stimulus output until capture occurs in a predetermined number of cardiac cycles. In one embodiment, the predetermined number of cardiac cycles is two. The stimulation threshold is then set to be equal to this stimulus output. Additional stimulus pulses are applied at stimulus outputs that are at least as great as this newly established stimulation threshold. Alternatively, the stimulus pulses are delivered at a predetermined level above the stimulation threshold. For example, additional stimulus pulses may be supplied to the heart 102 at levels at least 0.25 or 0.3 Volts above the stimulation threshold.

In the autothreshold mode, the stimulus output of the pulses is adjusted over a plurality of cardiac cycles. For example, in contrast to the autocapture mode, the stimulus output may not be adjusted on a beat-by-beat basis in the autothreshold mode. Instead, the stimulus output is adjusted over a plurality of cardiac cycles as described above.

As described above, the heart 102 may exhibit fusion-based behavior during the autocapture and/or autothreshold modes. Fusion can occur when delivery of a back-up ventricular stimulus pulse causes contraction of a ventricle (e.g., paced ventricular contraction) at approximately the same time that an atrial stimulus pulse is captured in the ventricle (e.g., intrinsic ventricular contraction). Fusion may cause the IMD 100 to miss the capture of a stimulus pulse in the ventricle in either the autocapture or autothreshold modes. As described above, fusion can cause the IMD 100 to perform unnecessary threshold searches in the autothreshold mode, thereby resulting in wasted electrical energy of the IMD 100 and potential discomfort to the patient. In order to avoid unnecessary threshold searches, the IMD 100 may automatically switch between the autocapture and autothreshold modes based on the detection of fusion-based behavior in the myocardium of the heart 102.

Figure 2:
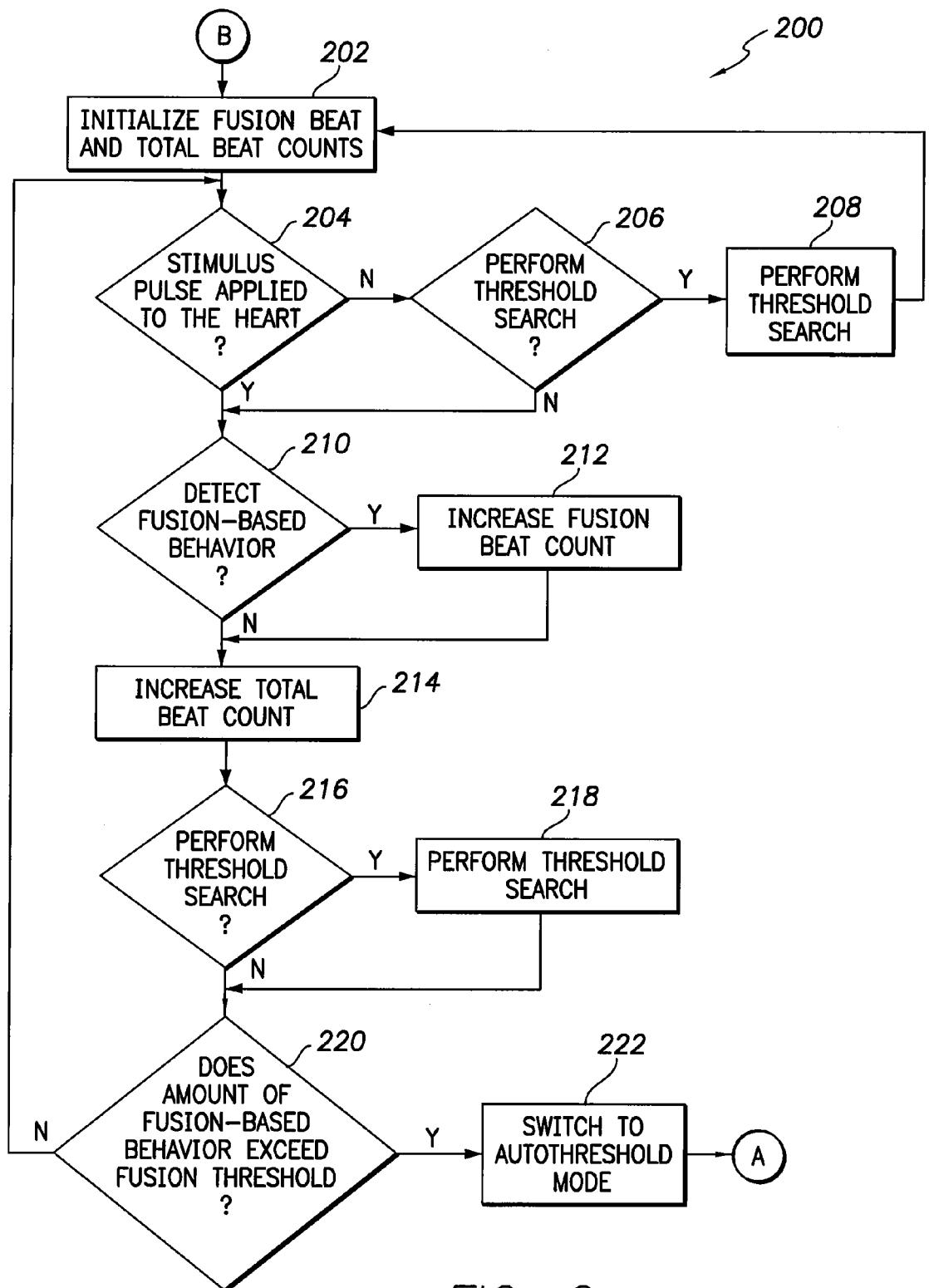
FIGS. 2 and 3 illustrate a flowchart of a method for automatically switching between autocapture and autothreshold modes of the IMD (shown in FIG. 1) in accordance with one embodiment.
Figure 3:
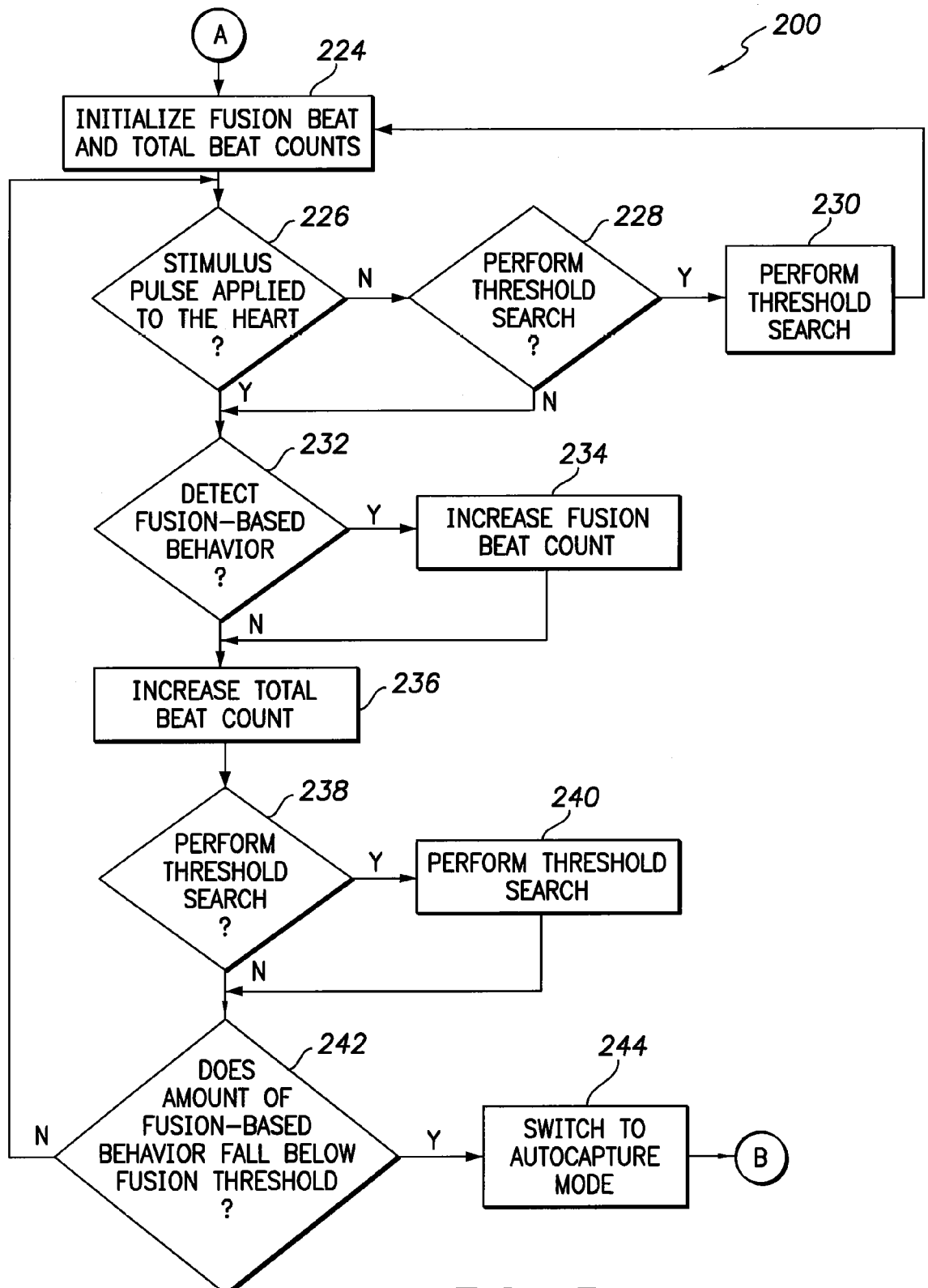

FIGS. 2 and 3 illustrate a flowchart of a method 200 for automatically switching between autocapture and autothreshold modes of the IMD 100 (shown in FIG. 1) in accordance with one embodiment. FIG. 2 illustrates operation of the IMD 100 in the autocapture mode while FIG. 3 illustrates operation of the IMD 100 in the autothreshold mode.

At 202, each of a fusion beat count and a total beat count is initialized. The fusion beat count is used to track an amount of fusion-based behavior occurring during each of the autocapture and autothreshold modes. For example, the fusion beat count may monitor the number of cardiac cycles in which fusion between paced and intrinsic contractions occur during a particular mode. The total beat count is used to track the total number of cardiac cycles occurring when in each of the autocapture and autothreshold modes. The fusion beat and total beat counts may be initialized by setting the values of the counts to zero or some other predetermined number.

Cardiac signals of the heart 102 (shown in FIG. 1) are monitored to determine when to deliver stimulus pulses to one or more chambers of the heart 102. The IMD 100 (shown in FIG. 1) may track cardiac signals over several cardiac cycles to identify when to apply a pacing stimulus pulse to the heart 102. By way of example only, the pacing stimulus pulse can be delivered to an atrium to maintain a cardiac rate or to correct unstable myocardial behavior.

At 204, a determination is made as to whether a stimulus pulse has been applied to a chamber of the heart 102 (shown in FIG. 1), such as a pacing pulse. If no stimulus pulse is applied during the current cardiac cycle, then the cardiac signals may not need to be tracked to determine whether fusion occurred during the current cardiac cycle. As a result, the flow of the method 200 continues to 206 to determine if a threshold search is due to be performed. At 206, a determination is made as to whether the IMD 100 (shown in FIG. 1) is due for a threshold search. For example, the IMD 100 may be programmed to perform a threshold search at least once every eight hours. Alternatively, a different time limit other than eight hours may be used. If no threshold search has been performed during the previous eight hours, then the IMD 100 conducts the threshold search at 208.

At 208, the threshold search is performed to adjust the stimulus output of subsequent stimulus pulses. As described above, the threshold search may include incrementally decreasing and/or increasing the electrical potential of the stimulus pulses over several cardiac cycles to adjust the electrical potential at which subsequent pulses are applied to the heart 102 (shown in FIG. 1). After the threshold search is completed, the flow of the method 200 returns to 202 where the fusion beat and total beat counters are initialized, as described above.

On the other hand, if, at 204, a stimulus pulse was applied to the heart 102 (shown in FIG. 1) or, at 206, the IMD 100 (shown in FIG. 1) was not due for a threshold search, then the flow of the method 200 continues to 210. Once a stimulus pulse is applied at 204 or at 206, an evoked response will occur. At 210, the evoked response of the heart 102 to the stimulus pulse is examined to determine if fusion occurs. The evoked response of the heart 102 may be examined by monitoring cardiac signals of the heart 102 after application of the stimulus pulse. For example, cardiac signals of the heart 102 can be monitored to identify whether a pacing pulse applied to a ventricle occurs concurrently with an intrinsic contraction of the ventricle. Polarization and/or depolarization of the ventricle take place over a time window or period. The pacing pulse and intrinsic contraction of the ventricle may concurrently occur with the polarization and/or depolarization of the ventricle when the pacing pulse is delivered during the same time window or period as the ventricular polarization and/or depolarization.

Figure 4:
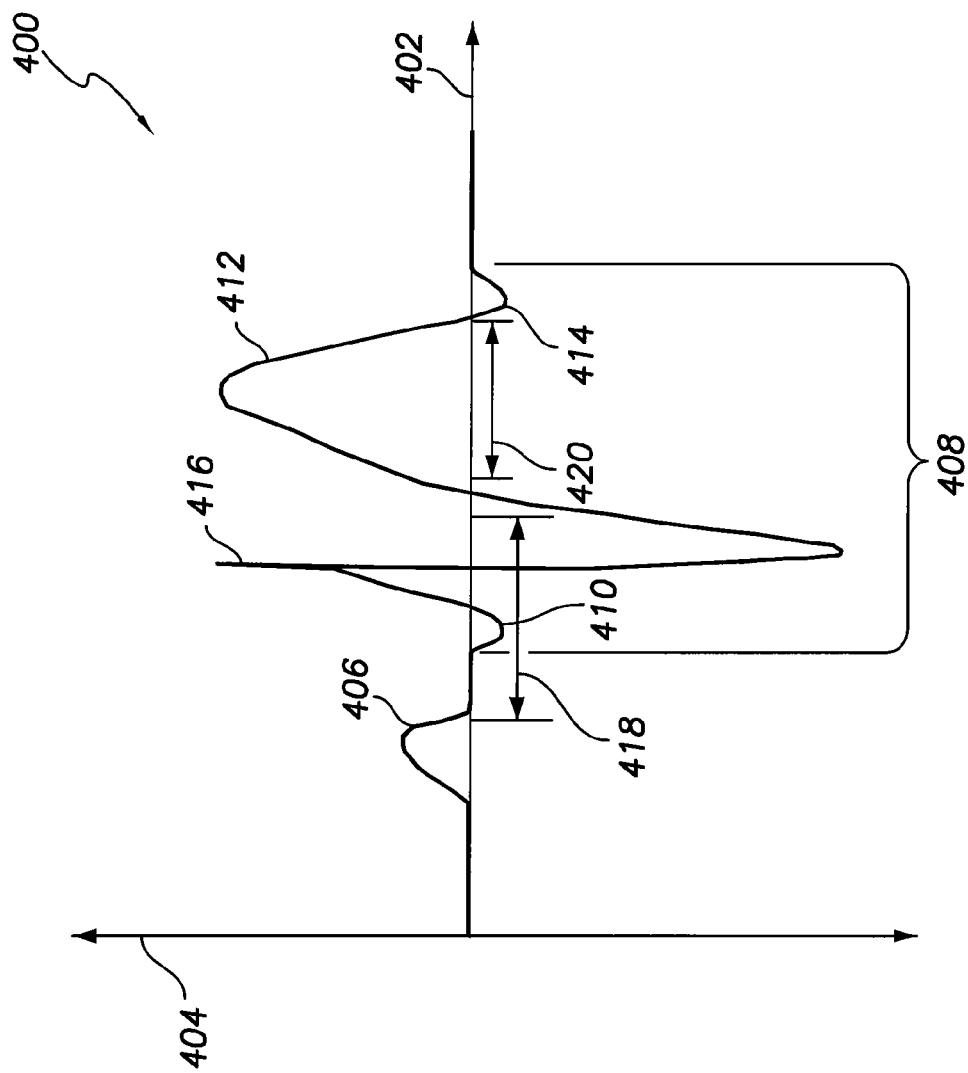
FIG. 4 illustrates an example of cardiac signals obtained over a single cardiac cycle.

FIG. 4 illustrates an example of cardiac signals 400 obtained over a single cardiac cycle and demonstrates the occurrence of fusion of a ventricular pacing pulse and an intrinsic ventricular contraction in accordance with one embodiment. The cardiac signals 400 may represent the signals monitored by the IMD 100 (shown in FIG. 1) after a stimulus pulse is applied at 204. For example, the cardiac signals 400 can include the evoked response of the heart 102 after a stimulus pulse is applied at 204. A QRS complex 408 in the cardiac signals is an evoked response of the heart 102 (shown in FIG. 1) to a stimulus pulse. As described above, the cardiac signals 400 are monitored at 210 to determine whether the heart 102 is exhibiting fusion-based behavior.

The cardiac signals 400 are shown alongside a horizontal axis 402 representative of time and a vertical axis 404 representative of the strength or magnitude of the cardiac signals 400. The cardiac signals 400 may be displaced above or below the horizontal axis 402 in other examples. The cardiac signals 400 include a P-wave 406 that is indicative of atrial polarization or contraction and the QRS complex 408 that represents ventricular polarization or contraction. The QRS complex 408 typically includes a Q-wave 410 that drops below the horizontal axis 402, an R-wave 412 that extends above the horizontal axis 402, and an S-wave 414 that dips slightly below the horizontal axis 402.

In the illustrated embodiment, a ventricular stimulus spike 416 is shown fused with the QRS complex 408. The ventricular stimulus spike 416 represents application of a stimulus pulse to a ventricle of the heart 102 (shown in FIG. 1). For example, if the IMD 100 (shown in FIG. 1) may supply a stimulus pulse to the heart 102 at 204. If the IMD 100 does not detect capture in the corresponding ventricle within a predetermined AV interval 418 after the P-wave 406, the IMD 100 delivers another stimulus pulse to the ventricle to ensure ventricular contraction during the cardiac cycle.

If the back-up stimulus pulse is applied before capture of the previous stimulus pulse in the ventricle (e.g., the occurrence of the QRS complex 408), the ventricular contractions caused by the back-up pulse and the previous stimulus pulse may become fused and conflated with one another. Fusion-based behavior of the heart 102 (shown in FIG. 1) may be identified based on the relative positions and/or shapes of waveforms of the cardiac signals obtained after delivery of the previous stimulus pulse. For example, with fusion-based behavior, the ventricular stimulus spike 416 may appear just after the onset of the QRS complex 408. Thus, in one embodiment, fusion-based behavior may be identified by determining whether a stimulus spike such as the ventricular stimulus spike 416 occurs after onset of another waveform such as the QRS complex 408.

In one embodiment, fusion-based behavior may be identified based on the shape of one or more waveforms. For example, a width 420 of the R-wave 412 may be indicative of fusion-based behavior. The width 420 of R-waves 412 may increase with fusion-based behavior. The width 420 of the R-wave 412 may be compared to a predetermined R-wave width to determine whether the width 420 is indicative of fusion-based behavior. If the width 420 exceeds the predetermined width, then the R-wave 412 may indicate that fusion has occurred. Alternatively, the width 420 may be compared to a function of previously measured R-wave widths of the heart 102. For example, the width 420 may be compared to an average, median, or other statistical function of previously measured R-wave widths. If the width 420 of the current cardiac cycle exceeds one or more of the average, median, and the like of a set of previously measured R-wave widths by a limit, then the width 420 may indicate that fusion has occurred.

Returning to the discussion of the method 200 shown in FIGS. 2 and 3 with continued reference to the cardiac signals 400 shown in FIG. 4, at 210, the evoked response of the heart 102 (shown in FIG. 1) is examined to determine whether the myocardium of the heart 102 demonstrates fusion-based behavior. The evoked response includes the cardiac signals of the heart 102 occurring after delivery of the stimulus pulse to the heart (at 204). As described above, the location and/or width of cardiac signal waveforms may be used to determine whether fusion has occurred. In one embodiment, the evoked response is examined at 210 to determine if the stimulus output of subsequent stimulus pulses needs to be increased. For example, the cardiac signals of the heart 102 after application of a stimulus pulse are monitored to determine if capture occurred in a ventricle. If no capture is detected, then the stimulus output of subsequent stimulus pulses may be increased by a predetermined amount.

At 212, when fusion-based behavior is detected in the current cardiac cycle at 210, then the fusion beat count is increased. The fusion beat count may be incrementally increased by one to indicate the occurrence of a cardiac cycle that includes fusion. At 214, the total beat count is increased. Similar to the fusion beat count, the total beat count may be incrementally increased by one to represent the occurrence of the cardiac cycle examined for fusion at 210. At 216, a determination is made as to whether to perform a threshold search. Similar to 206 described above, the IMD 100 may be programmed to perform a threshold search at least once every eight hours. If the IMD 100 is due for the threshold search, then the threshold search is performed at 218. If no threshold search is performed, or after the threshold search is performed at 218, the flow of the method 200 continues to 220.

At 220, the IMD 100 (shown in FIG. 1) examines the amount of fusion-based behavior detected during the autocapture mode to determine whether the IMD 100 should switch from the autocapture mode to the autothreshold mode. When the amount of fusion-based behavior exceeds one or more fusion thresholds, then the amount of fusion-based behavior may indicate that the frequency, at which fusion is occurring during the autocapture mode, is causing an unnecessary number of adjustments to the stimulus output. For example, the relatively frequent occurrence of fusion in the evoked response of the heart 102 (shown in FIG. 1) may cause the stimulus output of subsequent stimulus pulses to be adjusted on a beat-by-beat basis.

In one embodiment, at 220, the amount of fusion-based behavior is examined by comparing the fusion beat count with a predetermined minimum fusion beat count and by comparing a relation of the fusion beat count and total beat count with a predetermined threshold. The relation of the fusion beat count and the total beat count may be a ratio of the fusion beat count to the total beat count. By way of example only, if the fusion beat count exceeds the predetermined minimum fusion beat count and the ratio of the fusion beat count to the total beat count exceeds the predetermined threshold, then the amount of fusion-based behavior may indicate that the autocapture mode is adjusting the stimulus output too frequently. When the amount of fusion-based behavior exceeds the threshold at 220, flow continues to 222.

At 222, the mode of the IMD 100 (shown in FIG. 1) automatically switches from the autocapture mode to the autothreshold mode. In switching from the autocapture to autothreshold mode, the flow of the method 200 moves from 222 shown in FIG. 2 to 224 shown in FIG. 3. As described above, in accordance with one embodiment, the details of the autothreshold mode are shown in FIG. 3. When in the autothreshold mode, the IMD 100 may no longer monitor the evoked response of the heart 102 (shown in FIG. 1) to adjust the electrical potential of stimulus pulses on a beat-by-beat basis. For example, the IMD 100 may no longer adjust the electrical potential of a stimulus pulse for a subsequent cardiac cycle based on the evoked response of a preceding cardiac cycle.

Alternatively, if the amount of fusion-based behavior does not exceed the fusion thresholds, then the amount of fusion-based behavior may not indicate that the autocapture mode is adjusting the stimulus output too frequently. For example, if the fusion beat count does not exceed the predetermined minimum fusion beat count or the relation of the fusion beat count and the total beat count does not exceed the predetermined threshold, then the amount of fusion-based behavior may be insufficient to automatically switch the IMD 100 to the autothreshold mode. As a result, the flow of the method 200 returns to 204 where cardiac signals of the heart 102 (shown in FIG. 1) are examined to determine if a stimulus pulse has been applied to the heart 102, as described above.

With respect to the autothreshold mode described in connection with FIG. 3, at 224, the fusion beat and total beat counts are initialized, similar to as described above. Cardiac signals of the heart 102 (shown in FIG. 1) continue to be monitored to determine when to deliver stimulus pulses to one or more chambers of the heart 102.

At 226, a determination is made as to whether a stimulus pulse has been applied to a chamber of the heart 102 (shown in FIG. 1). If no stimulus pulse is applied during the current cardiac cycle, then the flow of the method 200 continues to 228 to determine if a threshold search is due to be performed. At 228, a determination is made as to whether the IMD 100 (shown in FIG. 1) is due for a threshold search, as described above. If no threshold search has been performed during the previous predetermined time period, then the IMD 100 conducts the threshold search at 230. At 230, the threshold search is performed to adjust the stimulus output of the stimulus pulses. After the threshold search is completed, the flow of the method 200 returns to 224 where the fusion beat and total beat counters are initialized, as described above. On the other hand, if, at 226, a stimulus pulse was applied to the heart 102 (shown in FIG. 1) or, at 228, the IMD 100 (shown in FIG. 1) was not due for a threshold search, then the flow of the method 200 continues to 232.

At 232, the evoked response of the heart 102 to the stimulus pulse is examined to determine if fusion occurs, as described above. The cardiac signals of the heart 102 (shown in FIG. 1) are monitored to identify whether the IMD 100 (shown in FIG. 1) applied a back-up stimulus pulse to the heart 102 at approximately the same time that the previous stimulus pulse was captured in the heart 102. At 234, if fusion-based behavior is detected in the current cardiac cycle, then the fusion beat count is increased. On the other hand, at 236, if fusion-based behavior is not detected in the current cardiac cycle, or after fusion-based behavior is detected and the fusion beat count is increased, the total beat count is increased. At 238, a determination is made as to whether to perform a threshold search. Similar to as described above, the IMD 100 may be programmed to perform a threshold search at least once every predetermined amount of time. If the IMD 100 is due for the threshold search, then the threshold search is performed at 240. If no threshold search is performed, or after the threshold search is performed at 240, the flow of the method 200 continues to 242.

At 242, the amount of fusion-based behavior detected during the autothreshold mode is examined to determine whether the IMD 100 (shown in FIG. 1) should switch from the autothreshold mode back to the autocapture mode. For example, if the amount of fusion-based behavior in the heart 102 (shown in FIG. 1) has sufficiently decreased, then the decrease in the fusion-based behavior may indicate that the IMD 100 can switch back to the autocapture mode. In one embodiment, the amount of fusion-based behavior is examined by comparing the amount of fusion-based behavior to one or more fusion thresholds, similar to as described above in connection with 220.

In one embodiment, the amount of fusion-based behavior is examined by determining if the fusion beat count falls below the predetermined minimum fusion beat count and if the ratio of the fusion beat count to the total beat count falls below the predetermined threshold described above. If the fusion beat count falls below the predetermined minimum fusion beat count and the ratio of the fusion beat count to the total beat count falls below the predetermined threshold, then the relatively small amount of fusion-based behavior may indicate that the IMD 100 (shown in FIG. 1) may automatically switch back to the autocapture mode. As a result, the flow of the method 200 continues to 244.

At 244, the mode of the IMD 100 (shown in FIG. 1) automatically switches from the autothreshold mode back to the autocapture mode. In switching from the autothreshold to autocapture mode, the flow of the method 200 moves from 244 shown in FIG. 3 back to 202 shown in FIG. 2. Alternatively, if the amount of fusion-based behavior does exceed the fusion thresholds, then the amount of fusion-based behavior may indicate that the fusion-based behavior continues to occur too frequently to switch back to the autocapture mode. For example, if the fusion beat count exceeds the predetermined minimum fusion beat count or the ratio of the fusion beat count to the total beat count exceeds the predetermined threshold, then the amount of fusion-based behavior may be too great to automatically switch the IMD 100 to the autocapture mode. As a result, the flow of the method 200 continues from 242 to 226 where cardiac signals of the heart 102 (shown in FIG. 1) are examined to determine if a stimulus pulse has been applied to the heart 102, as described above.

Figure 5:
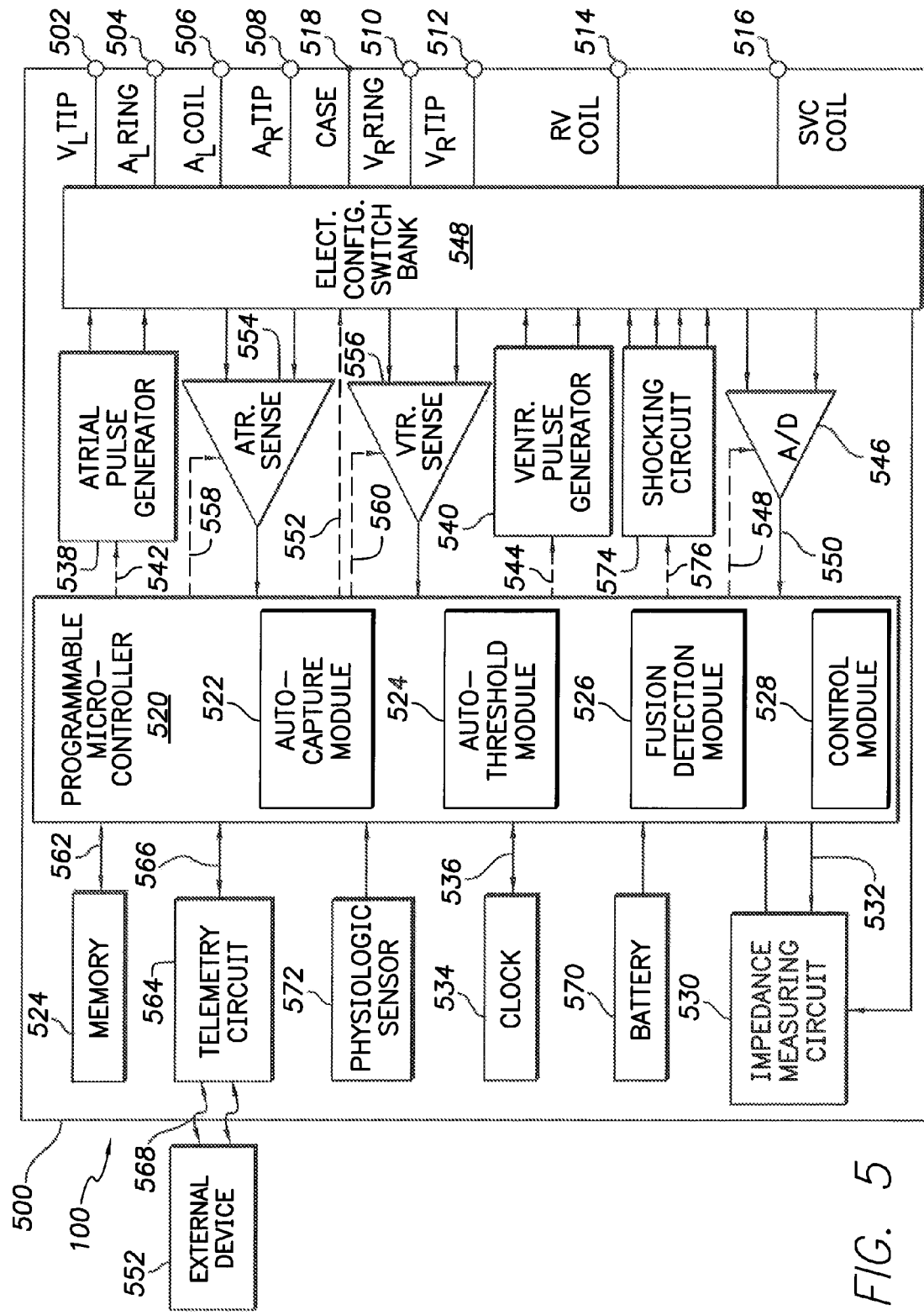
FIG. 5 illustrates a block diagram of exemplary internal components of the IMD shown in FIG. 1.

FIG. 5 illustrates a block diagram of exemplary internal components of the IMD 100. The IMD 100 includes the housing 500 that includes a left ventricle tip input terminal ($V_L$ TIP) 502, a left atrial ring input terminal ($A_L$ RING) 504, a left atrial coil input terminal ($A_L$ COIL) 506, a right atrial tip input terminal ($A_R$ TIP) 508, a right ventricular ring input terminal ($V_R$ RING) 510, a right ventricular tip input terminal ($V_R$ TIP) 512, an RV coil input terminal 514 and an SVC coil input terminal 516. A case input terminal 518 may be coupled with the housing 500 of the IMD 100. The input terminals 502-518 may be electrically coupled with the electrodes 112-128 (shown in FIG. 1).

The IMD 100 includes a programmable microcontroller 520, which controls the operation of the IMD 100. The microcontroller 520 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. The microcontroller 520 may include one or more modules and processors configured to perform one or more of the operations described above in connection with the method 200.

An autocapture module 522 senses evoked responses of the heart 102 (shown in FIG. 1) in response to delivery of stimulus pulses to the heart 102 when the IMD 100 operates in the autocapture mode described above. For example, the autocapture module 522 may examine the waveforms of cardiac signals sensed after supplying a stimulus pulse to an atrium of the heart 101. The autocapture module 522 may increase the electrical potential of stimulus pulses in subsequent cardiac cycles when an evoked response of a current cardiac cycle indicates a loss of capture, as described above.

An autothreshold module 524 performs threshold searches when the IMD 100 operates in the autothreshold mode described above. For example, the autothreshold module 524 may incrementally decrease the electrical potential of stimulus pulses delivered to myocardium of the heart 102 (shown in FIG. 1) until a loss of capture is detected in a first predetermined number of consecutive cardiac cycles. The autothreshold module 524 then may incrementally increase the electrical potential of the stimulus pulses until capture is detected in a second predetermined number of consecutive cardiac cycles. In one embodiment, the first and second predetermined numbers of consecutive cardiac cycles is two, although the first and second predetermined numbers of cardiac cycles may differ in another embodiment.

A fusion detection module 526 identifies fusion-based behavior in myocardium of the heart 102 (shown in FIG. 1). The fusion detection module 526 determines whether fusion occurs during a cardiac cycle. For example, the fusion detection module 526 may examine the position and/or shape of cardiac signal waveforms to identify fusion in a cardiac cycle, as described above. The fusion detection module 526 maintains the fusion beat count and the total beat count over predetermined intervals. In one embodiment, the fusion detection module 526 tracks the fusion beat count and the total beat count during the time period that the IMD 100 operates in each of the autocapture and autothreshold modes.

A control module 528 automatically switches the IMD 100 between the autothreshold and autocapture modes based on the presence of fusion-based behavior detected by the fusion detection module 526. For example, the control module 528 may switch the IMD 100 from the autocapture mode to the autothreshold mode when an amount of fusion-based behavior exceeds one or more fusion thresholds. In another example, the control module 528 switches the IMD 100 from the autothreshold mode to the autocapture mode when an amount of fusion-based behavior falls below one or more fusion thresholds. The control module 528 may base the decision whether to switch from one mode to the other on a number of cardiac cycles exhibiting fusion-based behavior, as described above.

The microprocessor 520 receives signals from the electrodes 112-128 (shown in FIG. 1) via an analog-to-digital (A/D) data acquisition system 546. The cardiac signals are sensed by the electrodes 112-128 and communicated to the data acquisition system 546. The cardiac signals are communicated through the input terminals 502-516 to an electronically configured switch bank, or switch, 548 before being received by the data acquisition system 546. The data acquisition system 546 converts the raw analog data of the signals obtained by the electrodes 120-138 into digital signals 550 and communicates the signals 550 to the microcontroller 520. A control signal 548 from the microcontroller 520 determines when the data acquisition system 546 acquires signals, stores the signals 550 in the memory 524, or transmits data to an external device 552.

The switch 548 includes a plurality of switches for connecting the desired electrodes 112-128 (shown in FIG. 1) and input terminals 502-518 to the appropriate I/O circuits. The switch 548 closes and opens switches to provide electrically conductive paths between the circuitry of the IMD 100 and the input terminals 502-518 in response to a control signal 552. An atrial sensing circuit 554 and a ventricular sensing circuit 556 may be selectively coupled to the leads 104-108 (shown in FIG. 1) of the IMD 100 through the switch 548 for detecting the presence of cardiac activity in the chambers of the heart 102 (shown in FIG. 1). The sensing circuits 554, 556 may sense the cardiac signals that are analyzed by the microcontroller 520. Control signals 558, 560 from the microcontroller 520 direct output of the sensing circuits 554, 556 that are connected to the microcontroller 520. An impedance measuring circuit 530 is enabled by the microcontroller 520 via a control signal 532. The impedance measuring circuit 530 may be electrically coupled to the switch 548 so that an impedance vector between any desired pairs of electrodes 120-138 may be obtained. The IMD 100 additionally includes a battery 570 that provides operating power to the circuits shown within the housing 500, including the microcontroller 520. The IMD 100 includes a physiologic sensor 572 that may be used to adjust pacing stimulation rate according to the exercise state of the patient.

A clock 534 may measure time relative to the cardiac cycles or cardiac signal waveforms of the heart 102 (shown in FIG. 1). The clock 534 measures elapsed amounts of time based on start and stop control signals 536 from the microcontroller 520 to determine the ventricular and atrial heart rates. Additionally, the clock 534 may track the amount of time elapsed between threshold searches. This elapsed time may be compared to a predetermined time period to determine whether to perform another threshold search, as described above.

The memory 524 may be embodied in a computer-readable storage medium such as a ROM, RAM, flash memory, or other type of memory. The microcontroller 520 is coupled to the memory 524 by a suitable data/address bus 562. The memory 524 may store programmable operating parameters and thresholds used by the microcontroller 520, as required, in order to customize the operation of IMD 100 to suit the needs of a particular patient. For example, the memory 524 may store data indicative of cardiac signal waveforms, the fusion thresholds, predetermined time periods, fusion beat counts, total beat counts, and the like. The operating parameters of the IMD 100 and thresholds may be non-invasively programmed into the memory 524 through a telemetry circuit 564 in communication with the external device 552, such as a trans-telephonic transceiver or a diagnostic system analyzer. The telemetry circuit 564 is activated by the microcontroller 520 by a control signal 566. The telemetry circuit 564 allows intra-cardiac electrograms, cardiac waveforms of interest, detection thresholds, status information relating to the operation of IMD 100, and the like, to be sent to the external device 552 through an established communication link 568.

Figure 6:
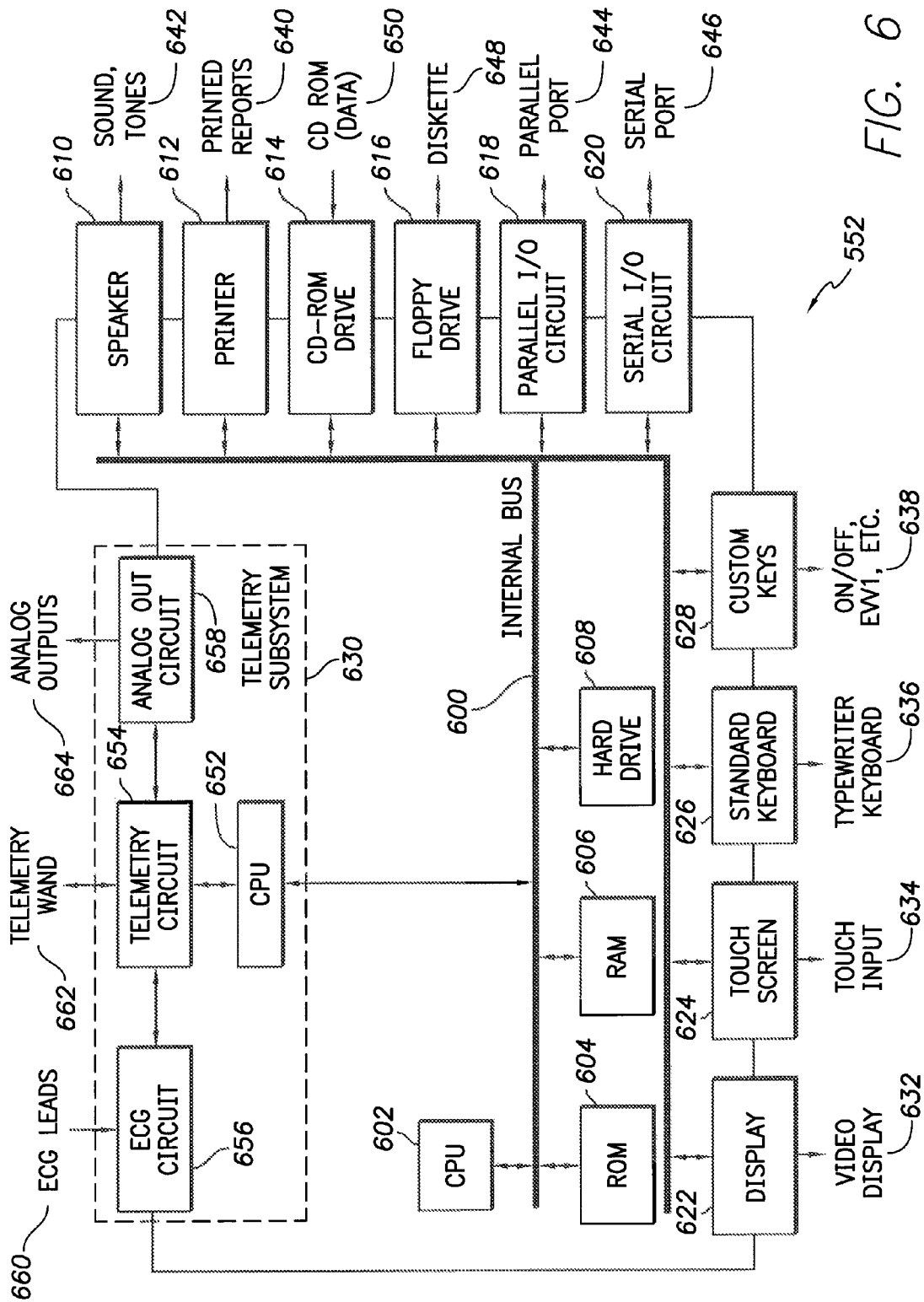
FIG. 6 illustrates a functional block diagram of an external device (shown in FIG. 5) that is operated to interface with the IMD (shown in FIG. 1).

FIG. 6 illustrates a functional block diagram of the external device 552, such as a programmer, that is operated to interface with the IMD 100 (shown in FIG. 1). The external device 552 includes an internal bus 600 that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus 600 is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 552 and with the IMD 100 (shown in FIG. 1). The CPU 602 may include RAM or ROM memory, logic and timing circuitry, state machine circuitry, and I/O circuitry to interface with the IMD 100. The display 622 (e.g., may be connected to the video display 632) and the touch screen 624 display graphic information relating to the IMD 100. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 552. The printer 512 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an ECG circuit 656 and an analog out circuit 658. The ECG circuit 656 is connected to ECG leads 660. The telemetry circuit 654 is connected to a telemetry wand 662. The analog out circuit 658 includes communication circuits to communicate with analog outputs 664. The external device 552 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 552 to the IMD 100 (shown in FIG. 1).

Figure 7:
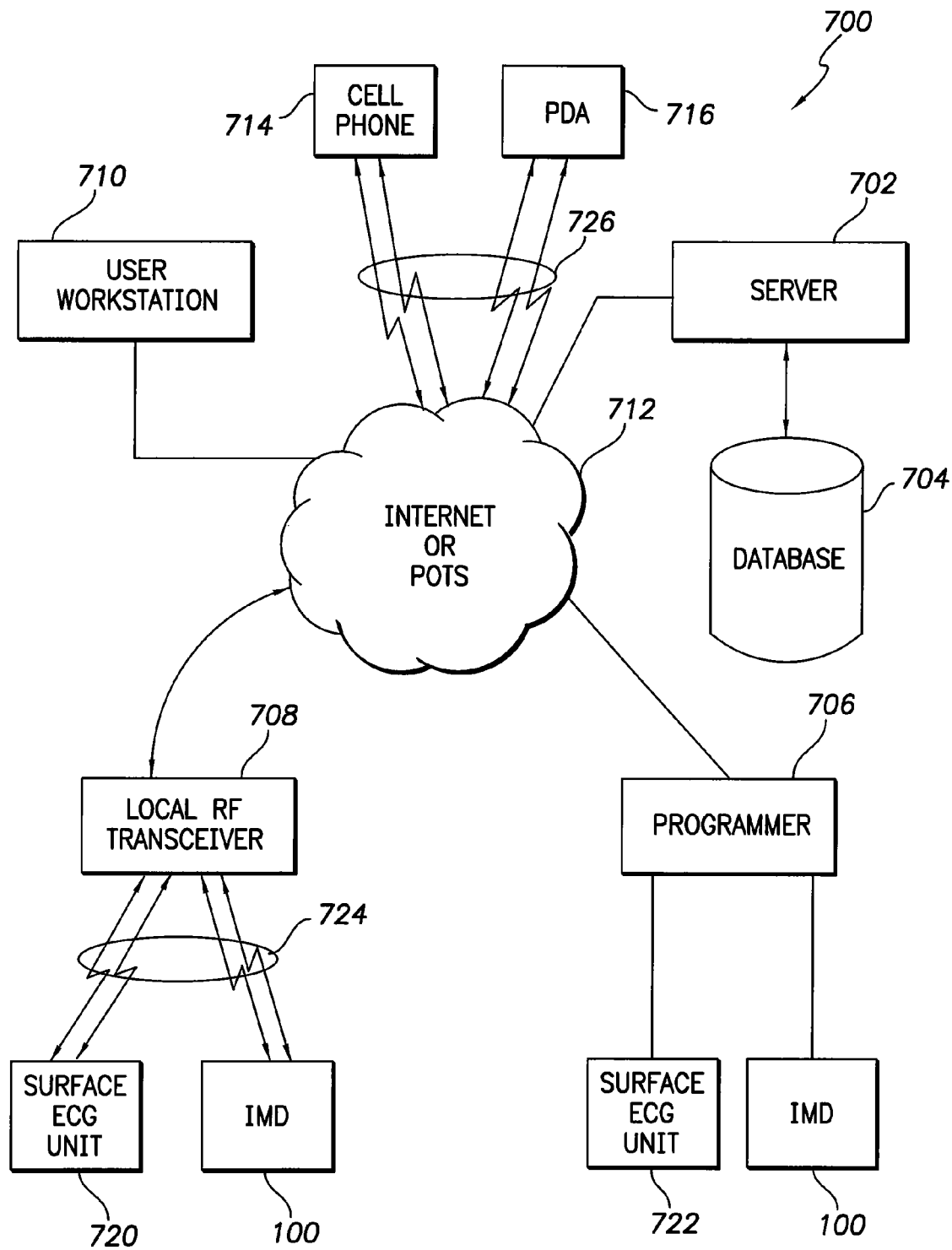
FIG. 7 illustrates a distributed processing system in accordance with one embodiment.

FIG. 7 illustrates a distributed processing system 700 in accordance with one embodiment. The distributed processing system 700 includes a server 702 connected to a database 704, a programmer 706 (e.g., similar to external device 552 (shown in FIG. 5)), a local RF transceiver 708 and a user workstation 710 electrically connected to a communication system 712. The communication system 712 may be the internet, a voice over IP (VoIP) gateway, a local plain old telephone service (POTS) such as a public switched telephone network (PSTN), a cellular phone based network, and the like. Alternatively, the communication system 712 may be a local area network (LAN), a campus area network (CAN), a metropolitan area network (MAN), or a wide area network (WAM). The communication system 712 serves to provide a network that facilitates the transfer/receipt of information such as cardiac signal waveforms, fusion thresholds, fusion beat counts, total beat counts, and the like.

The server 702 is a computer system that provides services to other computing systems over a computer network. The server 702 controls the communication of information such as cardiac signal waveforms, fusion thresholds, fusion beat counts, total beat counts, and the like. The server 702 interfaces with the communication system 712 to transfer information between the programmer 706, the local RF transceiver 708, the user workstation 710 as well as a cell phone 714 and a personal data assistant (PDA) 716 to the database 704 for storage/retrieval of records of information. On the other hand, the server 702 may upload raw cardiac signals from a surface ECG unit 720, 722 or the IMD 100 via the local RF transceiver 708 or the programmer 706.

The database 704 stores information such as cardiac signal waveforms, fusion thresholds, fusion beat counts, total beat counts, and the like, for a single or multiple patients. The information is downloaded into the database 704 via the server 702 or, alternatively, the information is uploaded to the server from the database 704. The programmer 706 is similar to the external device 552 and may reside in a patient's home, a hospital, or a physician's office. The programmer 706 interfaces with the surface ECG unit 722 and the IMD 100. The programmer 706 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 706 to the IMD 100. The programmer 706 is able to acquire cardiac signals from the surface of a person (e.g., ECGs), intra-cardiac electrogram (e.g., IEGM) signals from the IMD 100, and/or cardiac signal waveforms, fusion thresholds, fusion beat counts, total beat counts, and the like, from the IMD 100. The programmer 706 interfaces with the communication system 712, either via the internet or via POTS, to upload the information acquired from the surface ECG unit 720 or the IMD 100 to the server 702.

The local RF transceiver 708 interfaces with the communication system 712 to upload one or more of cardiac signal waveforms, ventricular and atrial heart rates, and detection thresholds 246 (shown in FIG. 2) to the server 702. In one embodiment, the surface ECG unit 720 and the IMD 100 have a bi-directional connection 724 with the local RF transceiver 708 via a wireless connection. The local RF transceiver 708 is able to acquire cardiac signals from the surface of a person, intra-cardiac electrogram signals from the IMD 100, and/or cardiac signal waveforms, fusion thresholds, fusion beat counts, total beat counts, and the like, from the IMD 100. On the other hand, the local RF transceiver 708 may download stored cardiac signal waveforms, fusion thresholds, fusion beat counts, total beat counts, and the like, from the database 704 to the surface ECG unit 720 or the IMD 100.

The user workstation 710 may interface with the communication system 712 via the internet or POTS to download cardiac signal waveforms, fusion thresholds, fusion beat counts, total beat counts, and the like via the server 702 from the database 704. Alternatively, the user workstation 710 may download raw data from the surface ECG units 720, 722 or IMD 100 via either the programmer 706 or the local RF transceiver 708. Once the user workstation 710 has downloaded the cardiac signal waveforms, ventricular and atrial heart rates, or detection thresholds 246, the user workstation 710 may process the information in accordance with one or more of the operations described above in connection with the method 200 (shown in FIG. 2). The user workstation 710 may download the information and notifications to the cell phone 714, the PDA 716, the local RF transceiver 708, the programmer 706, or to the server 702 to be stored on the database 704. For example, the user workstation 710 may communicate data to the cell phone 714 or PDA 716 via a wireless communication link 726.

Figure 8:
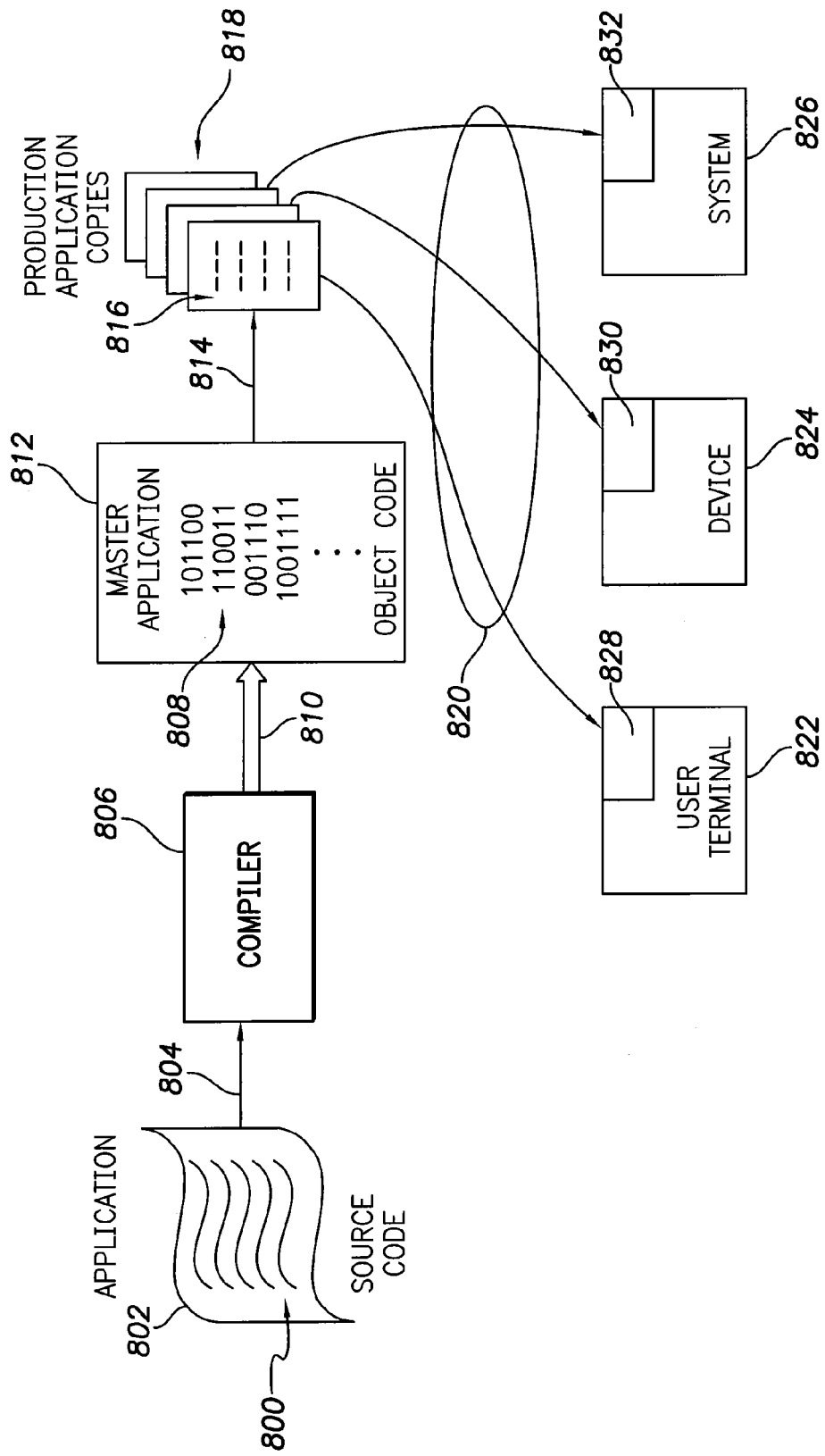
FIG. 8 illustrates a block diagram of example manners in which embodiments of the present invention may be stored, distributed, and installed on a computer-readable medium.

FIG. 8 illustrates a block diagram of example manners in which embodiments of the present invention may be stored, distributed, and installed on a computer-readable medium. In FIG. 8, the "application" represents one or more of the methods and process operations discussed above. The application is initially generated and stored as source code 800 on a source computer-readable medium 802. The source code 800 is then conveyed over path 804 and processed by a compiler 806 to produce object code 808. The object code 808 is conveyed over path 810 and saved as one or more application masters on a master computer-readable medium 812. The object code 808 is then copied numerous times, as denoted by path 814, to produce production application copies 816 that are saved on separate production computer-readable media 818. The production computer-readable media 818 are then conveyed, as denoted by path 820, to various systems, devices, terminals and the like.

A user terminal 822, a device 824 and a system 826 are shown as examples of hardware components, on which the production computer-readable medium 818 are installed as applications (as denoted by 828 through 832). For example, the production computer-readable medium 818 may be installed on the IMD 100 (shown in FIG. 1) and/or the microcontroller 520 (shown in FIG. 5). Examples of the source, master, and production computer-readable medium 802, 812, and 818 include, but are not limited to, CDROM, RAM, ROM, Flash memory, RAID drives, memory on a computer system, and the like. Examples of the paths 804, 810, 814, and 820 include, but are not limited to, network paths, the internet, Bluetooth, GSM, infrared wireless LANs, HIPERLAN, 3G, satellite, and the like. The paths 804, 810, 814, and 820 may also represent public or private carrier services that transport one or more physical copies of the source, master, or production computer-readable media 802, 812 or 818 between two geographic locations. The paths 804, 810, 814 and 820 may represent threads carried out by one or more processors in parallel. For example, one computer may hold the source code 800, compiler 806 and object code 808. Multiple computers may operate in parallel to produce the production application copies 816. The paths 804, 810, 814, and 820 may be intra-state, inter-state, intra-country, inter-country, intra-continental, inter-continental, and the like.

The operations noted in FIG. 8 may be performed in a widely distributed manner world-wide with only a portion thereof being performed in the United States. For example, the application source code 800 may be written in the United States and saved on a source computer-readable medium 802 in the United States, but transported to another country (corresponding to path 804) before compiling, copying and installation. Alternatively, the application source code 800 may be written in or outside of the United States, compiled at a compiler 806 located in the United States and saved on a master computer-readable medium 812 in the United States, but the object code 808 transported to another country (corresponding to path 814) before copying and installation. Alternatively, the application source code 800 and object code 808 may be produced in or outside of the United States, but production application copies 816 produced in or conveyed to the United States (for example, as part of a staging operation) before the production application copies 816 are installed on user terminals 822, devices 824, and/or systems 826 located in or outside the United States as applications 828 through 832.

As used throughout the specification and claims, the phrases "computer-readable medium" and "instructions configured to" shall refer to any one or all of (i) the source computer-readable medium 802 and source code 800, (ii) the master computer-readable medium and object code 808, (iii) the production computer-readable medium 818 and production application copies 816 and/or (iv) the applications 828 through 832 saved in memory in the terminal 822, device 824, and system 826.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable medical device comprising:
a lead including electrodes configured to be positioned within a heart, at least one of the electrodes being capable of sensing cardiac signals;
a pulse generator configured to deliver a stimulus pulse through at least one of the electrodes;
an autocapture module configured to sense an evoked response after delivery of the stimulus pulse when operating in an autocapture mode;
an autothreshold module configured to perform a threshold search when operating in an autothreshold mode;
a fusion detection configured module to identify fusion-based behavior in the heart; and
a control module to automatically switch between the autothreshold and autocapture modes based on a presence of the fusion-based behavior.

2. The implantable medical device of claim 1, wherein the control module automatically switches from the autocapture mode to the autothreshold mode when an amount of the fusion-based behavior exceeds a fusion threshold.

3. The implantable medical device of claim 1, wherein the control module automatically switches from the autothreshold mode to the autocapture mode when an amount of the fusion-based behavior falls below a fusion threshold.

4. The implantable medical device of claim 1, wherein the control module automatically switches between the autothreshold and autocapture modes based on a number of cardiac cycles exhibiting fusion-based behavior.

5. The implantable medical device of claim 1, wherein the fusion detection module maintains a fusion beat count of a number of cardiac cycles exhibiting fusion-based behavior and a total count of cardiac cycles over a predetermined interval, the control module automatically switching between the autothreshold and autocapture modes based on the fusion beat count and the total count.

6. The implantable medical device of claim 1, wherein the autocapture module increases an output of a stimulus pulse delivered during a subsequent cardiac cycle when the evoked response indicates a loss of capture.

7. The implantable medical device of claim 1, wherein the threshold search includes incrementally decreasing an output of stimulus pulses delivered to the heart until a loss of capture is detected in a first predetermined number of consecutive cardiac cycles and incrementally increasing the output of the stimulus pulses until capture is detected in a second predetermined number of consecutive cardiac cycles.

8. A method for automatically switching between autocapture and autothreshold modes in an implantable medical device, the method comprising:
delivering a stimulus pulse to a heart;
identifying fusion-based behavior in the heart in response to the stimulus pulse;
automatically switching between the autocapture and autothreshold modes based on a presence of the fusion-based behavior;
when in the autocapture mode, sensing an evoked response after delivery of a stimulus pulse; and
when in the autothreshold mode, performing a threshold search.

9. The method of claim 8, wherein the automatically switching operation comprises changing from the autocapture mode to the autothreshold mode when an amount of the fusion-based behavior exceeds a fusion threshold.

10. The method of claim 8, wherein the automatically switching operation comprises changing from the autothreshold mode to the autocapture mode when an amount of the fusion-based behavior falls below a fusion threshold.

11. The method of claim 8, wherein the automatically switching operation comprises alternating between the autothreshold and autocapture modes based on a number of cardiac cycles exhibiting fusion-based behavior.

12. The method of claim 8, further comprising maintaining a fusion beat count of a number of cardiac cycles exhibiting fusion-based behavior and a total count of cardiac cycles over a predetermined interval, wherein the automatically switching operation comprises alternating between the autothreshold and autocapture modes based on the fusion beat count and the total count.

13. The method of claim 8, further comprising, when in the autocapture mode, increasing an output of a stimulus pulse delivered during a subsequent cardiac cycle when the evoked response indicates a loss of capture.

14. The method of claim 8, further comprising, when in the autothreshold mode, incrementally decreasing an output of stimulus pulses delivered to the heart until a loss of capture is detected in a first predetermined number of consecutive cardiac cycles and incrementally increasing the output of the stimulus pulses until capture is detected in a second predetermined number of consecutive cardiac cycles.

15. A non-transitory computer readable storage medium for an implantable medical device having a lead with electrodes configured to be positioned within a heart to sense cardiac signals, a pulse generator, and a microcontroller, the non-transitory computer readable storage medium comprising instructions:
to direct the pulse generator to deliver a stimulus pulse to the heart; and
to direct the microcontroller to:
identify fusion-based behavior in the heart in response to the stimulus pulse;
automatically switch between an autocapture mode and an autothreshold mode based on a presence of the fusion-based behavior;
when in the autocapture mode, sense an evoked response after delivery of the stimulus pulse; and
when in the autothreshold mode, perform a threshold search.

16. The non-transitory computer readable storage medium of claim 15, wherein the instructions direct the microcontroller to automatically switch from the autocapture mode to the autothreshold mode when an amount of the fusion-based behavior exceeds a fusion threshold.

17. The non-transitory computer readable storage medium of claim 15, wherein the instructions direct the microcontroller to automatically switch from the autothreshold mode to the autocapture mode when an amount of the fusion-based behavior falls below a fusion threshold.

18. The non-transitory computer readable storage medium of claim 15, wherein the instructions direct the microcontroller to automatically switch alternate between the autothreshold and autocapture modes based on a number of cardiac cycles exhibiting fusion-based behavior.

19. The non-transitory computer readable storage medium of claim 15, wherein the instructions direct the microcontroller to maintain a fusion beat count of a number of cardiac cycles exhibiting fusion-based behavior and a total count of cardiac cycles over a predetermined interval, further wherein the instructions direct the microcontroller to alternate between the autothreshold and autocapture modes based on the fusion beat count and the total count.

20. The non-transitory computer readable storage medium of claim 15, wherein, when the microcontroller is in the autocapture mode, the instructions direct the pulse generator to increase an output of a stimulus pulse delivered during a subsequent cardiac cycle when the evoked response indicates a loss of capture.

* * * * *